(12) United States Patent
Dreher

(10) Patent No.: US 8,097,288 B1
(45) Date of Patent: Jan. 17, 2012

(54) COMPOSITION AND METHOD FOR PROVIDING NUTRITIONAL IMMUNOLOGY FOR PRODUCTION ANIMALS

(75) Inventor: Mark Dreher, Woodland Hills, CA (US)

(73) Assignee: POM Wonderful, LLC, Los Angeles, CA (US)

( * ) Notice: Subject to any disclaimer, the term of this patent is extended or adjusted under 35 U.S.C. 154(b) by 91 days.

(21) Appl. No.: 12/425,171

(22) Filed: Apr. 16, 2009

Related U.S. Application Data

(60) Provisional application No. 61/045,592, filed on Apr. 16, 2008.

(51) Int. Cl.
*A61K 36/00* (2006.01)

(52) U.S. Cl. .......................... 424/777; 424/725; 424/442

(58) Field of Classification Search .................. None
See application file for complete search history.

(56) References Cited

U.S. PATENT DOCUMENTS

| | | | |
|---|---|---|---|
| 5,958,423 A * | 9/1999 | Chu ........................... | 424/202.1 |
| 6,387,418 B1 | 5/2002 | Aviram et al. | |
| 6,641,850 B1 | 11/2003 | Aviram et al. | |
| 6,977,089 B1 | 12/2005 | Aviram et al. | |
| 2006/0057235 A1 | 3/2006 | Aviram et al. | |
| 2006/0269629 A1 | 11/2006 | Bates et al. | |
| 2008/0057143 A1 * | 3/2008 | Madjid ........................ | 424/769 |

OTHER PUBLICATIONS http://www.vetoquinol.ca/en/index.asp?page=14—accessed 9/10.*
Unpublished U.S. Appl. No. 11/745,440, filed Jul. 5, 2007 "Oral or Enteral Dosage Forms Containing Phytochemicals from Pomegranates" to Anderson et al.
Seeram et al. "Bioavailability of ellagic acid in human plasma after consumption of ellagitannins from pomegranate (*Punica granatum* L.) juice", Clinica Chimica Acta 348 (2004) 63-68.
Seeram, et al., "Pomegranate Juice Ellagitannin Metabolites Are Present in Human Plasma and Some Persist in Urine for Up to 48 Hours", Journal of Nutrition, 2006, 2481-2485.
Seeram, et al. "Pomegranate Juice and Extracts Provide Similar Levels of Plasma and Urinary Ellagitannin Metabolites in Human Subjects" Journal of Medicinal Food, 11 (2) 2008, 390-394.
D. Syed, et al. "Photochemopreventive Effect of Pomegranate Fruit Extract on UVA-mediated Activation of Cellular Pathways in Normal Human Epidermal Keratinocytes" Photochemistry and Photobiology, 2006, 82: 398-405.
Adams, et al. "Pomegranate Juice, Total Pomegranate Ellagitannins, and Punicalagin Suppress Inflammatory Cell Signaling in Colon Cancer Cells" Journal of Agricultural and Food Chemistry, 2006, 54, 980-985.
V. Adhami, et al. "Polyphenols from green tea and pomegranate for prevention of prostate cancer" Free Radical Research, Oct. 2006; 40(10): 1095-1104.

S. Kasimsetty, et al. "Effects of Pomegranate Chemical Constituents/Intestinal Microbial Metabolites on CYP1B1 in 22Rv1 Prostate Cancer Cells" Journal of Agriculture and Food Chemistry, 2009, 57, 10636-10644.
Sartippour, et al., "Ellagitannin-rich pomegranate extract inhibits angiogenesis in prostate cancer in vitro and in vivo" International Journal of Oncology, 2008, 32:475-480.
Rettig, et al. "Pomegranate extract inhibits androgen-independent prostate cancer growth through a nuclear factor-KB-dependent mechanism" Molecular Cancer Therapy, 2008; 7(9): 2662-71.
Seeram, et al."Pomegranate Ellagitannin-Derived Metabolites Inhibit Prostate Cancer Growth and Localize to the Mouse Prostate Gland" Journal of Agricultural and Food Chemistry, 2007, 55, 7732-7737.
Hong, et al. "Pomegranate polyphenols down-regulate expression of androgen-synthesizing genes in human prostate cancer cells overexpressing the androgen receptor" Journal of Nutritional Biochemistry, 2008, 8 pages.
J. Khateeb, et al. "Paraoxonase 1 (PON1) expression in hepatocytes is upregulated by pomegranate polyphenols: A role for PPAR" Atherosclerosis, 2009, 7 pages.
M. Davidson, et al. "Effects of Consumption of Pomegranate Juice on Carotid Intima-Media Thickness in Men and Women at Moderate Risk for Coronary Heart Disease" American Journal of Cardiology, 2009, 936-942.
O. Rozenberg, et al. Pomegranate juice sugar fraction reduces macrophage oxidative state, whereas white grape juice sugar fraction increases it Atherosclerosis, 188 (2006) 68-76.
Mattiello, et al. "Effects of Pomegranate Juice and Extract Polyphenols on Platelet Function" Journal of Medicinal Food, 12 (2) 2009, 7 pages.
Sumner, et al. "Effects of Pomegranate Juice Consumption on Myocardial Perfusion in Patients With Coronary Heart Disease" American Journal of Cardiology, 2005, 5 pages.
M. Aviram, et al. "Pomegranate Phenolics from the Peels, Arils, and Flowers Are Antiatherogenic: Studies in Vivo in Atherosclerotic Apolipoprotein E-Deficient (E0) Mice and in Vitro in Cultured Macrophages and Lipoproteins" Journal of Agricultural and Food Chemistry, 2008, 56, 1148-1157.
Shiner et al. "Macrophage paraoxonase 2 (PON2) expression is upregulated by pomegranate juice phenolic anti-oxidants via PPAR and AP-1 pathway activation" Atherosclerosis, 2007, 9 pages.
de Nigris, et al. "Effects of a Pomegranate Fruit Extract rich in punicalagin on oxidation-sensitive genes and eNOS activity at sites of perturbed shear stress and atherogenesis" Cardiovascular Research, 2007, 73, 414-423.

(Continued)

Primary Examiner — Susan Hoffman
(74) Attorney, Agent, or Firm — Cotman IP Law Group, PLC

(57) ABSTRACT

A method of reducing an involuntary cull in production animals. The method comprising the step of administering to the production animals a composition comprising an effective amount of a pomegranate extract substantially derived from the whole fruits of pomegranate. The pomegranate extract can be in powder, liquid or solid form and mixed into foods as part of a regular regime of the production animals diet. When site specific treatment is needed such as with mastitis in milk cows the pomegranate extract may be injected directly to the site where treatment is desired.

17 Claims, 6 Drawing Sheets

OTHER PUBLICATIONS de Nigris, et al."Pomegranate juice reduces oxidized low-density lipoprotein downregulation of endothelial nitric oxide synthase in human coronary endothelial cells" Nitric oxide, 2006 15 259-263.

L. Ignarro, et al. "Pomegranate juice protects nitric oxide against oxidative destruction and enhances the biological actions of nitric oxide" Nitric oxide, 2006, 15, 93-102.

de Nigris et al. "Beneficial effects of pomegranate juice on oxidation-sensitive genes and endothelial nitric oxide synthase activity at sites of perturbed shear stress" Proceedings of the National Academy of Sciences, 2005, vol. 102, No. 13, 6 pages.

Rosenblat, et al. "Pomegranate Byproduct Administration to Apolipoprotein E-Deficient Mice Attenuates Atherosclerosis Development as a Result of Decreased Macrophage Oxidative Stress and Reduced Cellular Uptake of Oxidized Low-Density Lipoprotein" Journal of Agricultural and Food Chemistry, 2006, 54, 1928-1935.

de Nigris, et al. "The influence of pomegranate fruit extract in comparison to regular pomegranate juice and seed oil on nitric oxide and arterial function in obese Zucker rats" Nitric Oxide, 2007 17, 50-54.

Fuhrman, et al. "Pomegranate juice inhibits oxidized LDL uptake and cholesterol biosynthesis in macrophages" Journal of Nutritional Biochemistry, 2005, 16, 570-576.

Kaplan, et al. "Pomegranate Juice Supplementation to Atherosclerotic Mice Reduces Macrophage Lipid Peroxidation, Cellular Cholesterol Accumulation and Development of Atherosclerosis" Journal of Nutrition, 2001, 2082-2089.

M. Aviram, et al. "Pomegranate juice consumption for 3 years by patients with carotid artery stenosis reduces common carotid intima-media thickness, blood pressure and LDL oxidation" Clinical Nutrition, 2004, 23, 423-433.

M. Abu Zaid, et al. "Inhibition of UVB-mediated Oxidative Stress and Markers of Photoaging in Immortalized HaCaT Keratinocytes by Pomegranate Polyphenol Extract POMx" Photochemistry and Photobiology, 2007, 83: 882-888.

Lorean et al. "Maternal Dietary Supplementation with Pomegranate Juice Is Neuroprotective in an Animal Model of Neonatal Hypoxic-Ischemic Brain Injury" Pediatric Research, 2005, vol. 57, No. 6, 7 pages.

Shah, et al. "Pomegranate juice decreases amyloid load and improves behavior in a mouse model of Alzheimer's disease" Neurobiology of Disease, 2006, Abstract.

D. Bialonska, et al. "Urolithins, Intestinal Microbial Metabolites of Pomegranate Ellagitannins, Exhibit Potent Antioxidant Activity in a Cell-Based Assay" Journal of Agriculture and Food Chemistry, 2009, 57, 10181-10186.

Y. Zhang, et al. "Absence of Pomegranate Ellagitannins in the Majority of Commercial Pomegranate Extracts: Implications for Standardization and Quality Control" Journal of Agricultural and Food Chemistry, 2009, 57, 7395-7400.

Y. Zhang, et al. "International Multidimensional Authenticity Specification (IMAS) Algorithm for Detection of Commercial Pomegranate Juice Adulteration", Journal of Agricultural and Food Chemistry, 2009, 9 pages.

S. Madrigal-Carballo, et al. "Pomegranate (*Punica granatum*) supplements: authenticity, antioxidant and polyphenol composition" Journal of Functional Foods, 2009, 6 pages.

K. Martin et al. "Development of a novel pomegranate standard and new method for the quantitative measurement of pomegranate polyphenols" Journal of Science of Food and Agriculture, 2009; 89:157-162.

N. Seeram, et al. "Comparison of Antioxidant Potency of Commonly Consumed Polyphenol-Rich Beverages in the United States" Journal of Agricultural and Food Chemistry, 2008, 56, 1415-1422.

Gil et al. "Antioxidant Activity of Pomegranate Juice and Its Relationship with Phenolic Composition and Processing" Journal of Agricultural and Food Chemistry, 2000, 48, 4581-4589.

M. Haidari, et al. "Pomegranate(*Punicagranatum*) purified polyphenol extract inhibits influenza virus and has a synergistic effect with oseltamivir" Phytomedicine, 2009, 10 pages.

M. Reddy, et al. "Antioxidant, Antimalarial and Antimicrobial Activities of Tannin-Rich Fractions, Ellagitannins and Phenolic Acids from *Punica granatum* L." Planta Medica, 2007, 7 pages.

M. Shukla, et al. "Consumption of hydrolyzable tannins-rich pomegranate extract suppresses inflammation and joint damage in rheumatoid arthritis" Nutrition, 24, 2008, 733-743.

Z. Rasheed, et al. "Polyphenol-rich pomegranate fruit extract (POMx) suppresses PMACI-induced expression of pro-inflammatory cytokines by inhibiting the activation of MAP Kinases and NF-κB in human KU812 cells" Journal of Inflammation, 2009, 12 pgs.

Glycaemic Index Research Service "A Study to Measure the Glycaemic Index Value of Pomegranate Juice" The School of Molecular and Microbial Bio-sciences at Sydney University, Mar. 2009, 22 pgs.

B. McFarlin, et al. "Pomegranate seed oil consumption during a period of high-fat feeding reduces weight gain and reduces type 2 diabetes risk in CD-1 mice" British Journal of Nutrition, 2008, 6 pages.

W. Rock, et al. "Consumption of Wonderful Variety Pomegranate Juice and Extract by Diabetic Patients Increases Paraoxonase 1 Association with High-Density Lipoprotein and Stimulates Its Catalytic Activities" Journal of Agricultural and Food Chemistry, 2008, 56, 8704-8713.

M. Rosenblat, et al. "Anti-oxidative effects of pomegranate juice (PJ) consumption by diabetic patients on serum and on macrophages" Atherosclerosis, 187 (2006) 363-371.

K. Azadzoi, et al."Oxidative Stress in Arteriogenic Erectile Dysfunction: Prophylactic Role of Antioxidants" Journal of Urology, 2005, vol. 174, 386-393.

Forest, et al. "Efficacy and safety of pomegranate juice on improvement of erectile dysfunction in male patients with mild to moderate erectile dysfunction: a randomized, placebo-controlled, double-blind, crossover study" International Journal of Impotence Research, 2007, 1-4.

S. Strum, et al. "Pomegranates and Prostate Health: A Research Report", PCRI Insights, 2008, vol. 11: No. 3, 36 pages.

A. McCutcheon, et al. "Scientific and Clinical Monograph for POM Wonderful Pomegranate Juice" American Botanical Council, 2008, 20 pgs.

M. Aviram, et al. "Pomegranate juice flavonoids inhibit low-density lipoprotein oxidation and cardiovascular diseases: Studies in atherosclerotic mice and in humans" Drugs Under Experimental and Clinical Research XXVIII, 2003, 15 pages.

M. Warren, et al. "Pomegranate's Ancient Roots to Modern Medicine, Pomegranates: Ancient Roots to Modern Medicine" Taylor and Francis, 2006, 158-166.

D. Heber, et al. "Safety and Antioxidant Activity of a Pomegranate Ellagitannin-Enriched Polyphenol Dietary Supplement in Overweight Individuals with Increased Waist Size" Journal of Agricultural and Food Chemistry, 2007, 55, 10050-10054.

D. Farkas, et al. "Pomegranate Juice Does Not Impair Clearance of Oral or Intravenous Midazolam, a Probe for Cytochrome P450-3A Activity: Comparison With Grapefruit Juice" Journal of Clinical Pharmacology, 2007; 47;286-294.

F. Afaq, et al. "Protective effect of pomegranate-derived products on UVB-mediated damage in human reconstituted skin" Experimental Dermatology, 2009.

D Pérez et al., Wine, Diet, Antioxidant Defenses and Oxidative Damage. Annals of the New York Academy of Sciences (2002),957:136-145.

KJ Joshipura, et al., The Effect of Fruit and Vegetable Intake on Risk for Coronary Heart Disease. Annals of Internal Medicine (2001),134:1106-1114.

http://www.wonderfulpomegranateresearch.com/featured, Jun. 2011.

* cited by examiner

A

B

Standard Chromatogram of Punicalin, Punicalagin A&B and Ellagic Acid at 360 nm

Chromatogram of POMx at 360 nm

Chromatogram of POMx at 280 nm

COMPOSITION AND METHOD FOR PROVIDING NUTRITIONAL IMMUNOLOGY FOR PRODUCTION ANIMALS

This application claims benefit of U.S. Provisional Patent Application Ser. No. 61/045,592 filed Apr. 16, 2008 the specification of which is hereby incorporated herein by reference.

BACKGROUND OF THE INVENTION

1. Field of the Invention

One or more embodiments of the invention described herein pertain to the manufacture and use of pomegranate compositions in an animal diet to achieve beneficial effects such as an increased rate of weight gain and/or decreased involuntary cull rate.

2. Description of the Related Art

Efficient digestion and/or rumination in production animals is important to maximize feed intake, feed efficiency, production of milk, meat or other animal product, and maintaining acceptable level of milk components. Having a healthy digestive and/or rumen environment reduces the risk and incidence of metabolic disorders that can occur with improper feeding management or abrupt feed intake changes.

The current practice in the production animal industry, which may include beef and dairy cattle, is to allow the animals to self-feed. Having a self-feeding nutrition management program means that all or part of an animal's complete diet is placed in feeder equipment so that the animal has free access to the food at all times of the day over the entire feeding period. Hence with a self-feeding program the animals self regulate their food intake quantity.

In a self-feeding program economic losses may result when the animals decrease their food intake, develop erratic feed consumption habits or decrease their feeding efficiencies. Such behaviors sometimes lead to decreased animal asset production (e.g., milk, beef, offspring), reduced animal health, and an increase in animal deaths. To manage such issues one current technique is to make use of the practice of culling to reduce herd size. If done effectively and with the correct timing, culling is an economic decision that can lead to improved animal asset production and herd profitability. There are many reasons for culling animals, and some of those reasons are loosely separated into "voluntary culling" and "involuntary culling."

Voluntary culling traditionally includes those production animals that leave the herd due to, for example, low milk production in the absence of disease, or those sold into other producers' herd. Involuntary culling is loosely defined as "those production animal that leave the herd against the wishes of the producer." Examples of non-voluntary culling include being physically impaired (e.g., injury, crippled), persistent health problems, non-breeding, disease or death.

The biological and market factors surrounding a culling decision are both complex and unpredictable. The dynamic nature of such factors includes uncertainty regarding future productivity and economic value of the herd. Involuntary culling is a major economic problem in the production animal industry. Every time a production animal is culled, the producer incurs a cash cost. The cash cost of the cull is simply the price of the replacement animal minus the salvage value of the culled animal.

The Food and Drug Administration (FDA) first approved the sub-therapeutic and therapeutic use of antibiotics for farm animals in 1951. The use of antibiotics improved animal health by treating disease and improving animal productivity. Such antibiotics were administered by adding doses to the production animal's feed or water supply. However, public concerns about the potential for antibiotic-resistant microbes to develop in production animals and transfer to humans have led to restrictions in the practice of administering antibiotics.

To prevent over usage of antibiotics in production animals various regulatory agencies have taken action. In one example of a regulatory response, the European Union recently mandated that antibiotics may not be used as growth promoters in feed animals. Over the years, antibiotics have been slowly restricted, culminating with the complete banning of antibiotics in the European Union as growth promoters commencing Jan. 1, 2006. There is both a political move and a public health concern with the use of antibiotics as feed additives.

The restriction or banning of antibiotic supplements in animal diets has a direct cost in terms of economics and animal health. The commercial cost of producing meat and milk from animals has increased and the health of the animals in high-density production facilities has decreased.

For at least the limitations described above there is a need for natural and economical methods for decreased culling rates, increased body scores, increased milk production, and the improvement of welfare in production animals.

BRIEF SUMMARY OF THE INVENTION

One or more embodiments of the invention are directed to a method for administering an effective amount of pomegranate extract to improve overall health and decrease an involuntary cull rate in production animals. Compositions other in addition to the pomegranate extract may be included in conjunction with the pomegranate extract. The term production animal as used herein refers to livestock as well as other animals that are used as a source of food, for producing food or accomplishing work.

In at least one embodiment of the invention the composition used as a supplement to the production animal diet contains an effective amount of pomegranate extract. The benefits of administering the composition having pomegranate extract may include but are not limited to: increased animal weight gain; increased relative quantities of beneficial microbes in the animal; decreased relative quantities of malicious microbes in the animal; increased uptake of beneficial minerals, nutrients and vitamins; improved general health of the animal; replacement of sub-therapeutic doses of antibiotics in animal feed; and/or, reduced or eliminated doses of antibiotic in animal feed.

In cases where the production animals are dairy cows increased milk production is achieved by administering an effective amount of pomegranate extract in accordance with one or more embodiments of the invention. While the invention is described and illustrated here in the context of production animals such as dairy cows readers should not that the same beneficial effect may be achieved in domestic animals and hence the invention is not limited solely to production animals but may encompass other animals.

The effective amount of pomegranate extract is administered to the production animals using a self-feeding approach but other ways of administering appropriate amounts of extract are considered within the scope and spirit of the invention. For example in cases where an animal's food intake is lower than it should be the concentration of pomegranate extract may be increased to make sure the animal is given an effective amount on a regular basis. Food intake may also be restricted if needed to maintain animal health. Delivery of the pomegranate extract in solid, powder and liquid forms does not change the effects described here and as such administration of the pomegranate extract in any form is contemplated for maintaining health and growth in production animals.

The composition used in accordance with one or more embodiments of the invention serves as a nutritional supplement that increases weight gain and reduces diarrhea morbidity, mortality and severity by stimulation of natural immune response, provides nutritional support of immune function in a manner that is easily mixed, standardized, stored, transported, measured and re-suspended. Pomegranate extract is included in diet of production animals to enhance the animal's immune response.

In one embodiment of the invention pasture forage is treated with pomegranate extract as a delivery mechanism. When cattle or lambs are grazed on forage treated with pomegranate extract, immune function is preserved or depressed immune function is reversed.

Other methods of delivery such as injection of the pomegranate extract at or near a site of injury is also an approach for reducing the effect of infection due to bacteria or viruses. An injection approach is feasible in that compositions containing an effective amount of pomegranate extract are suitable for being transferred into natural body cavities of mammals, such as the teat canal of a dairy cow; and accidental skin cavities caused by injury such as cuts, burns and disease. The compositions can be applied, for instance, to body cavities or openings. The compositions provide the prevention of intrusion of infection-causing microorganisms. In dairy cows for example a reduction in mastitis or other bacteria related ailments may be achieved through injecting pomegranate extract into the infected area. Performing such injections prevents the contamination of a teat canal of a dairy cow from infections by environmental mastitis related microorganisms. Simultaneously, the composition having pomegranate extract can also sanitize, disinfect, prevent inflammation, and promote healing of the interior walls of a body cavity or body opening. Such sanitizing/disinfecting activity occurs without requiring the inclusion of antimicrobial and/or antibiotics agents, however any composition may include such additional agents.

BRIEF DESCRIPTION OF THE DRAWINGS

The above and other aspects, features and advantages of one or more embodiments of the invention will be more apparent from the following more particular description thereof, presented in conjunction with the following drawings wherein.

Figure 4:
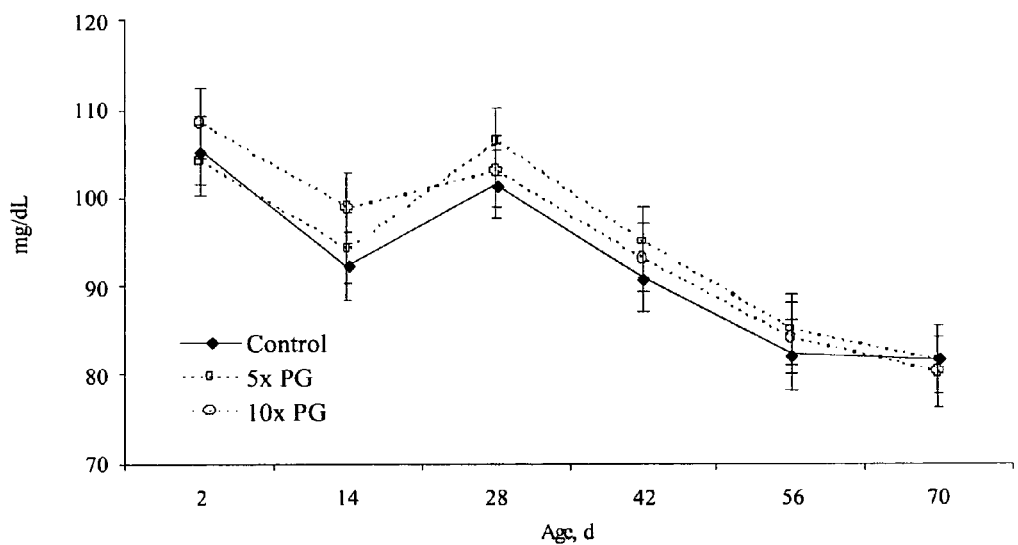
Figure 4:
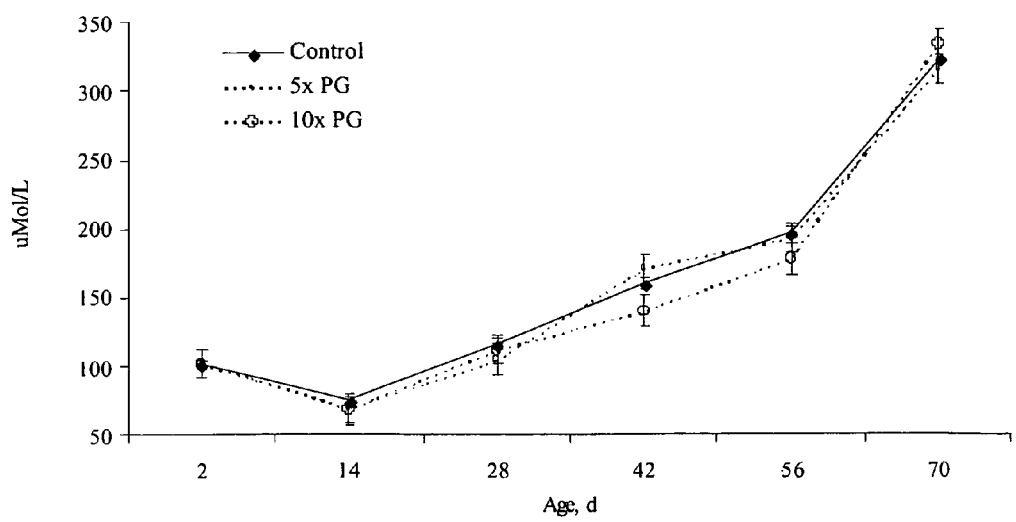

Panels A and B in FIG. 4 illustrate the effect of feeding pomegranate extract to calves on the rumen fermentation and development. Plasma concentrations of glucose (Panel A; mg/dL) and BHBA (panel B; μMol/L) in calves fed 0 (Control), 5 (5×) or 10 g/d (10×) of pomegranate extract containing 10% polyphenols. For glucose, treatment ($P=0.65$), age ($P<0.001$), interaction between treatment and age ($P=0.97$). Orthogonal polynomial responses to treatment: Linear ($P=0.41$); quadratic ($P=0.70$). For BHBA, treatment ($P=0.55$), age ($P<0.001$), interaction between treatment and age ($P=0.69$). Orthogonal polynomial responses to treatment: Linear ($P=0.28$); quadratic ($P=0.92$).

Figure 5:
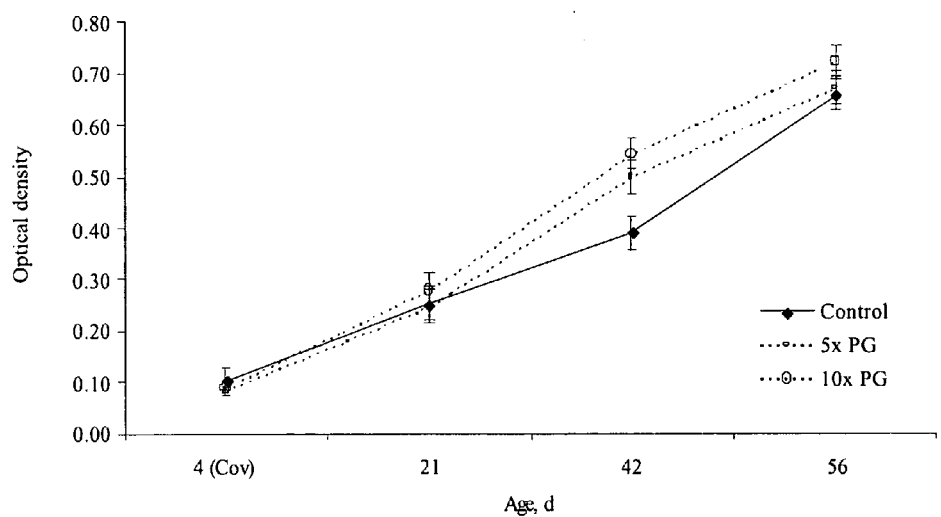

FIG. 5 illustrate the effect of feeding pomegranate extract to animals on immune functions and humoral immunity. Anti-ovalbumin (OVA) IgG titers in serum (optical density) of calves fed 0 (control), 5 (5×) or 10 g/d (10×) of pomegranate extract containing 10% polyphenols. Measurement on d 4 served as covariate (Coy). Effect of treatment ($P=0.02$), age ($P<0.0001$), and interaction between treatment and age ($P=0.04$). Orthogonal polynomial responses to treatment: Linear ($P=0.004$); quadratic ($P=0.93$).

Figure 6:
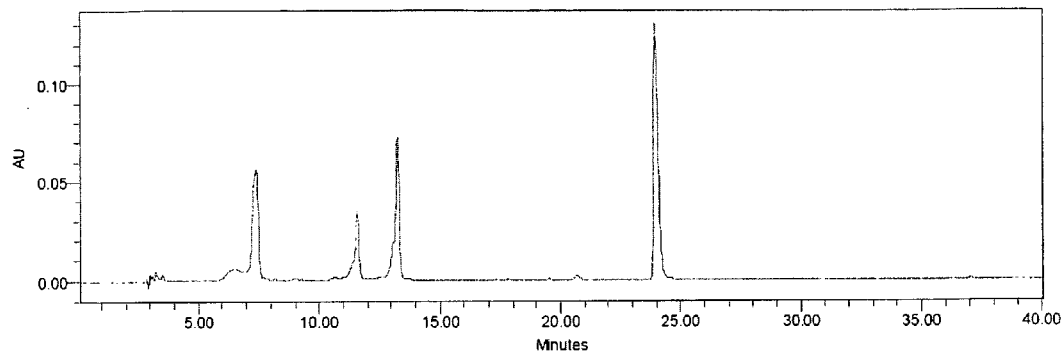
Figure 6:
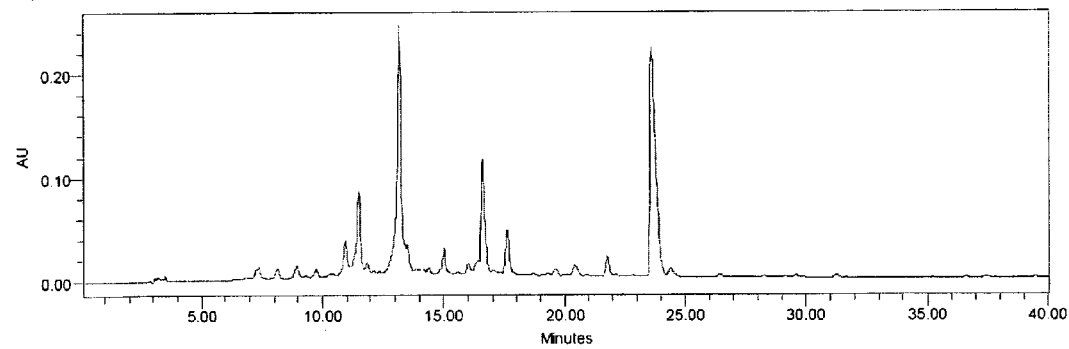
Figure 6:
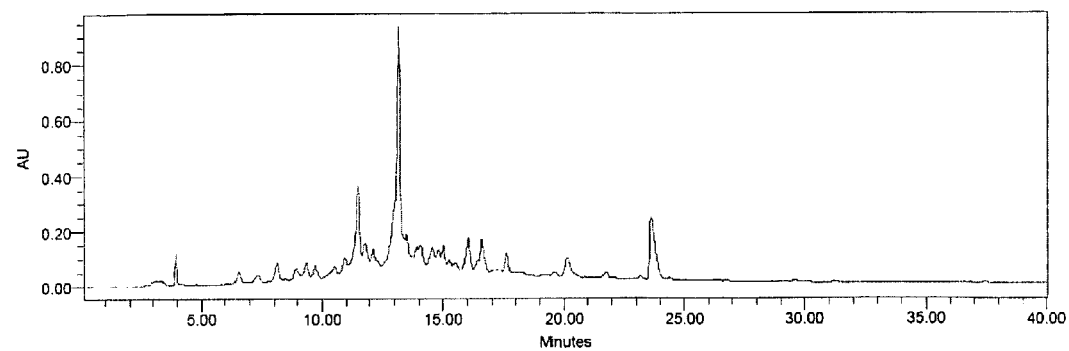

FIG. 6 illustrates a series of chromatograms showing a standard of punicalin, punicalagin A & B and Ellagic Acid, against the profile for the pomegranate extract POMx™ made using the pomegranate Wonderful variety.

DETAILED DESCRIPTION

A composition and method for initiating an improved immune response in production animals will now be described. In the following exemplary description numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

The following patents, patent applications, and publications are incorporated herein by reference: U.S. patent application Ser. No. 09/294,307 (filed Apr. 19, 1999); U.S. patent application Ser. No. 09/998,883 (filed Nov. 19, 2001); U.S. patent application Ser. No. 10/701,918 (filed Nov. 4, 2003); U.S. patent application Ser. No. 11/252,842 (filed Oct. 18, 2005); U.S. patent application Ser. No. 60/784,861 (filed Mar. 21, 2006); U.S. patent application Ser. No. 11/137,248 (filed May 24, 2005); U.S. patent application Ser. No. 60/782,437 (filed Mar. 15, 2006); and, U.S. patent application Ser. No. 11/745,440 (filed May 7, 2007).

Pomegranate extract as used in one or more embodiments of the invention are substantially derived from whole fruits of pomegranate, including the arils, the pericarp, the inner membrane and the seeds. The pomegranate extract may be derived from pomegranate solids such as the pericarp, inner membrane and seeds of the pomegranate. Pomegranate extract, as obtained from the pomegranate solids is beneficial in that it has a higher total polyphenol content than is found in the juice from the pomegranate arils. This is particularly true with respect to the higher molecular weight polyphenols, including punicalagin. In addition to punicalagin, other high molecular weight polyphenols, including ellagitannin and other hydrolysable tannins, are more prevalent in the extract derived from pomegranate solids. One process that yields pomegranate extract that may be used in one or more embodiments of the invention is fully described in the U.S. Application No. 20060269629, which is hereby incorporated herein by reference. Readers should note however that while use of a pomegranate extract derived from pomegranate solids is generally more effective due the presence of a higher level of polyphenols. Hence while other pomegranate extracts may work effectiveness is measured by the quantity of polyphenols rather than the quantity of pomegranate extract. As a result pomegranate extracts with lower levels of polyphenols may require higher quantities to achieve the effect described here. Table 3 shows a side-by-side comparison of the concentration of the polyphenols punicalagins, punicalin, ellagic acid glycosides, and ellagic acid in an exemplary pomegranate extract and the pomegranate juice.

TABLE 3

| Compound Name | Extract (mg/ml) | Juice from Arils (mg/ml) | Ratio |
|---|---|---|---|
| Punicalagin (β-isomer) | 4.79 | 0.02 | 239.5 |
| Punicalagin (α-isomer) | 21.80 | 0.15 | 145.3 |
| Punicalin | 3.62 | NA | — |
| Ellagic Acid Glycosides | 19.65 | 0.33 | |
| Ellagic Acid | 18 | 0.74 | |
| Total polyphenols: | 67.86 | 1.24 | 54.7 |

Although other polyphenols are present in both the pomegranate extract and juice, and this example highlights the unexpected and surprising results in that significantly higher concentrations of polyphenols, particularly of punicalagin, are present in the pomegranate extract than in the pomegranate juice. Table 3 shows that although the exemplary extract has 54.7 times the total polyphenols than pomegranate juice from arils, the extract has a substantially pucacalin.

Pomegranate extract contains polyphenols, including hydrolysable tannins and flavonoids. Pomegranate extract of the varietal used in one or more embodiments of the invention (e.g., the Wonderful variety of *Punica Granatum*) comprises principally hydrolysable tannins, a lesser amount of flavonoids, and a much smaller amount of ellagic acid. As a group, the family of pomegranate polyphenol tannins found in pomegranate extract, while large and diverse, is comprised of a relatively small number of building blocks that vary in number of repeating units and combinations. These building blocks are based, in part, on glucose as a sugar and gallic acid as the simplest phenolic monomer (glycone). When gallic acid dimerizes, the two bound molecules form ellagic acid. When ellagic acid dimerizes, it forms gallagic acid, which is essentially four gallic acids. When glucose is incorporated into the structure, gallotannins and ellagitannins are formed. As the complexity or size of the molecule increases, a large combination of the simple building blocks form an array of polyphenol tannins such as ellagitannins (based on repeating units of ellagic acid) and gallotannins (based on repeating units of gallic acid). Collectively, the various combinations form oligomers, which are short polymers consisting of only a few monomer units (gallic acid or ellagic acid or a combination). Punicalin is a monomeric hydrolysable polyphenol containing gallagic acid and glucose. Punicalagin is a monomeric hydrolysable polyphenol containing gallagic acid, ellagic acid and glucose.

Figure 1:
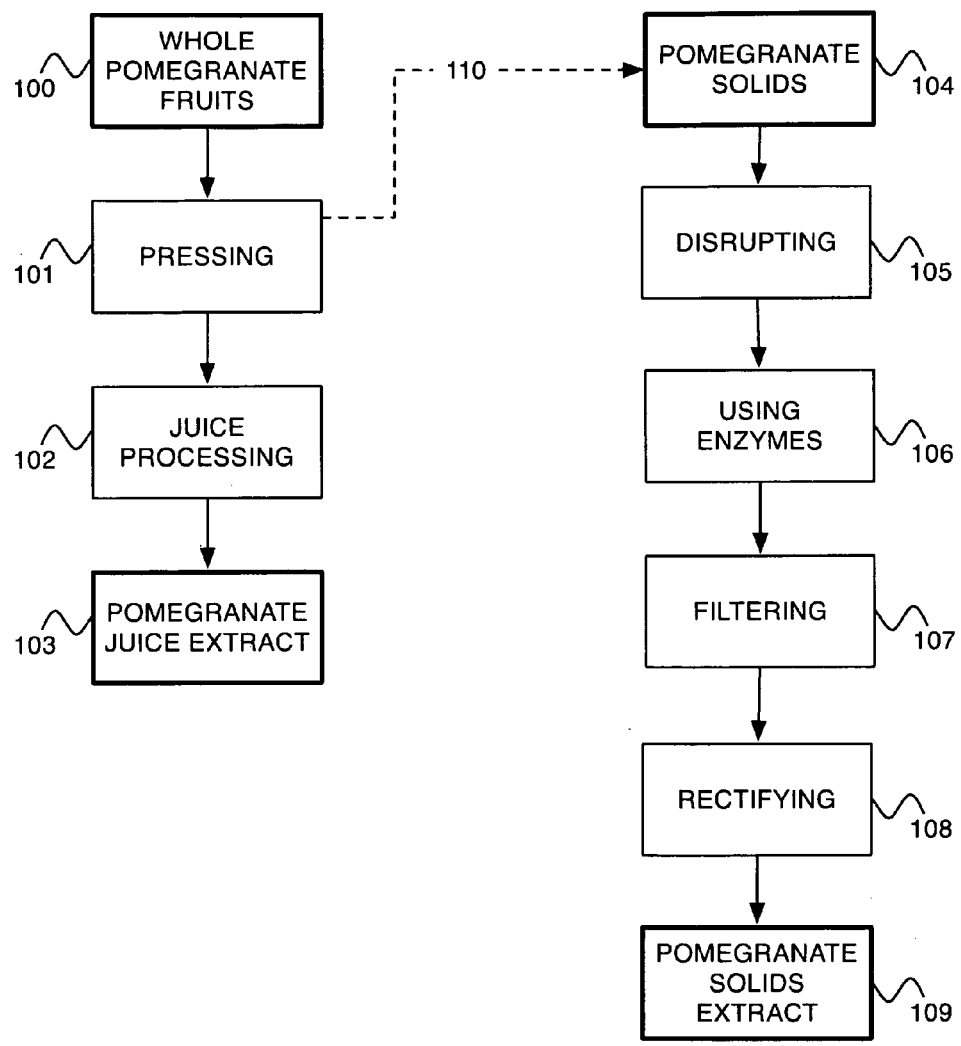
FIG. 1 illustrates some embodiments of the process of obtaining pomegranate extract.

FIG. 1 illustrates the process of obtaining pomegranate extract to administer for achieving the desired effect. Pomegranate extract in the form of juice 103 is obtained from the whole fruits of pomegranate 100 which undergo a pressing step 101 that extract juices by bearing an external pressure against the whole fruits in ways that such juice is expelled therefrom. Any method of forcing juices out of the whole fruits, including crushing and grinding qualifies as pressing step 101. The insoluble residues left over after pressing step 101 are pomegranate solids 104 which are further processed to make other forms of pomegranate extract with a higher total polyphenol content. The resulting pressed juice 101 undergoes juice processing step 102 which may filter out solid residues, pasteurizes and optionally concentrates the pressed juice to obtain pomegranate juice or pomegranate juice concentrate 103 as pomegranate extract.

Pomegranate solids 104 may undergo a disrupting step 105 to create a grind of pomegranate solids. The disrupting step may use any method to produce rough grind or fine particles of pomegranate solids, include milling or crushing. The mixture of disrupted pomegranate solids are dispersed in an aqueous solution which may then optionally undergo an using enzymes step 106 to liberate phytochemicals from the plant tissues and/or cells. Such enzymes may include any one or a combination of pectinase, cellulase, hemicellulase, amylase, arabinase, and other hydrolyzing enzymes, to name a few. After enzymes have at least partially degraded the pomegranate solids, the residual insoluble materials may be removed from the mixture through filtering step 107. In one or more embodiments of the invention the enzyme step may be skipped depending upon the desired Filtering step 107 may be accomplished by filtration, centrifugation, chromatographic techniques, and any other techniques to extract phytochemicals from pomegranate solids. The resulting extract from filtering step 107 undergoes rectifying step 108 using any method to concentrate, dry or refine the resulting extract to produce pomegranate extract 109.

The method of one or more embodiments of the invention is applicable to any mammal. Examples of the type of mammal to which the method may be applied include production animals, laboratory animals, including rodents such as mice, rats and guinea pigs; farm animals such as cows, sheep, pigs and goats; companion animals such as dogs and cats; and primates such as monkeys, apes and humans. However, other animals may also benefit from practicing one or more embodiments of the invention in particular animals that are used to produce a product such as milk or eggs. In addition to production animals other high value animals such as horses and fur animals such as mink also benefit from administration of the composition referenced herein.

Through administration of the pomegranate composition one or more embodiments of the invention provides a method for decreasing an involuntary cull rate in production animals, wherein the involuntary cull generally results from infection, disease, morbidity, or mortality. The method generally comprises administering to production animals a composition containing an effective amount of pomegranate extract.

According to one embodiment, the pomegranate extract is provided as an additive to production animal feed that may be used at any or all stages of animal development. The pomegranate extract may, for example, be added or mixed into the feed as a concentrated raw product, a concentrated raw product with a protein, raw product absorbed into a matrix, and/or a concentrated raw product with a protein absorbed into a matrix. The pomegranate extract may also be administered in powder, liquid concentrate, or juice form. In cases where use of the extract is site specific administration may be achieved through injection of a liquid concentrate into the production animal.

The term "cull" as used herein is generally defined as the removal of an animal from the herd, litter, flock, and the like. The term "involuntary culling" as used herein refers to the removal of an animal from the herd because of disease, illness, injury or death.

Many disorders or diseases arise from or are aggravated by oxidative stress and the presence of free radicals. The pomegranate extracts used in accordance with one or more embodiments of the invention are used to prevent, slow down or treat disorders associated with inadequate antioxidant levels and excess free radicals. Hence the various components within the pomegranate extract provide antioxidants that are useful for maintaining proper levels of antioxidants in the subject animal. This enables the treatment and/or prevention of a free radical induced disorder, an oxidative stress disorder, and/or for treatment of many disorders or diseases including the common cold and cancer through stimulation of the immune system and protection of the body against free radicals.

Non-limiting examples of disorders that arise due to altered (e.g., lowered) levels of antioxidants or damage from free radicals which is believed to contribute to the pathology of the disease state include, but are not limited to, inflammatory diseases, stroke, traumatic hemorrhage, gastric ulcers, low birth weight, lameness, sterility, depressed immune system, undesired cell apoptosis, myocardial infarction, mastitis, neoplasia, acidosis, metritis, feet and leg problems (e.g., laminitis, claw disease, digital dermatitis, and foot rot), rheumatoid arthritis, arthritis, low milk production, abnormal body weight, greasy pig disease, and heat-related stress.

Providing pomegranate extracts as described herein makes it feasible to boost the innate immune response of the production animals or other recipient. An "immunological response" to an antigen or pathogenic organism is the development in a mammal of a humoral and/or a cellular immune response. In one or more embodiments of the invention this immunological response is supported by the administration of pomegranate extract. A "humoral immune response" refers generally to an immune response mediated by antibody molecules, while a "cellular immune response" is generally one mediated by T-lymphocytes and/or other white blood cells. A "cellular immune response" also refers to the production of cytokines, chemokines and other such molecules produced by activated T-cells and/or other white blood cells, including those derived from CD4+ and CD8+ T-cells.

The innate immune system of mammals also recognizes and responds to molecular features of pathogenic organisms via activation of Toll-like receptors and similar receptor molecules on immune cells. Upon activation of the innate immune system, various non-adaptive immune response cells are activated to, e.g., produce various cytokines, lymphokines and chemokines Cells activated by an innate immune response include immature and mature dendritic cells of the moncyte and plamsacytoid lineage (MDC, PDC), as well as gamma, delta, alpha and beta T-cells and B-cells and the like. Thus, one or more embodiments of the invention also contemplates providing nutritional support for an immune response wherein the immune response involves both an innate and adaptive response. Such nutritional support comes from an effective amount of pomegranate extract weakening pathogenic organisms so that the immune system may do its job more effectively.

Pomegranate extract can be given to a mammal either after the onset of mastitis, thus serving as a treatment, or prior to the onset of mastitis, thus serving as a preventive measure. The preventive use of the subject invention is particularly important, for instance, in case mastitis has been detected in some animals in the same herd. It is often desirable to treat all animals in the same herd in order to eliminate the infection or risk of infection from the whole herd. Various delivery mechanisms are contemplated including oral and injected forms of the pomegranate extract.

Regardless of whether pomegranate extract is used to treat or prevent mastitis, the pomegranate extract can either be used individually or in combination with other pomegranate extracts. The pomegranate extract is administered either intramammarily or systemically.

When administered intramammarily in accordance with one or more embodiments of the invention, the pomegranate extract is administered by injection into the mammary gland, typically by infusion into the teat through the milk canal. The dosage of the pomegranate extract containing polyphenols by intramammary injection is from about 1,000 to 50,000 mg/l or 100-10,000 mg pomegranate extract per day.

When administered systemically, pomegranate extract is administered parenterally or orally, and typically once per day for three or more consecutive days.

When administered orally, pomegranate extract can be administered in tablet, capsule or liquid (suspension or solution) dosage form in a pharmaceutically acceptable vehicle. Pomegranate extract can also be administered in feed or drinking water. Oral administration in any of these dosage forms is well known in the art and may be carried out in ways common in the animal veterinary medical art. Regardless of the dosage form, the anti-mastitis effective amount of the pomegranate extract is from about 1,000 to 50,000 mg/l or 100-10,000 mg pomegranate extract per day.

When administered parenterally, pomegranate extract is administered by subcutaneous, intradermal, intramuscular, or intravenous injection. Parenteral administration is carried out in ways common in the animal veterinary or human medical art. When prepared as injectables, the pomegranate extract is usually prepared as liquid formulations in a pharmaceutically acceptable vehicle. Regardless of the route, the daily dosage of the pomegranate extract by parenteral administration is from about 1,000 to 50,000 mg/l or 100-10,000 mg pomegranate extract per day. The pomegranate extract utilized in one or more embodiments of the invention is the POM Wonderful varietal which is inclusive of a profile of hydrolysable tannins unique to this varietal. POMx™ is an extract made using the Wonderful variety of *Punica granatum* is a possible pomegranate extract to use in accordance with one or more embodiments of the invention. A series of chromatograms showing a standard of punicalin, punicalagin A & B and ellagic acid, against the profile for the pomegranate extract POMx™ made using the Wonderful variety is depicted at FIG. 6. The chromatograms were obtained from HPLC with a conventional C18 column with flow rate of 0.75 mL/min and mobile phase of a mixture of acetonitrile and 0.4% phosphate buffer in water.

The exact dosage and frequency duration of administration of pomegranate extract may be changed in response to numerous variables such as the particular pomegranate extract used, the severity of the condition being treated, the general physical condition of the animal, the response of the animal to the treatment, and the size of the animal. Hence the term effective dosage is measured by the effect on the production animal or subject rather than being specifically limited to a particular quantity as there is a range of quantities that are suitable for accomplishing the effect desired here.

The following non-limiting examples further illustrate embodiments of the invention.

Example 1

Preparation of Pomegranate Extract

Figure 2:
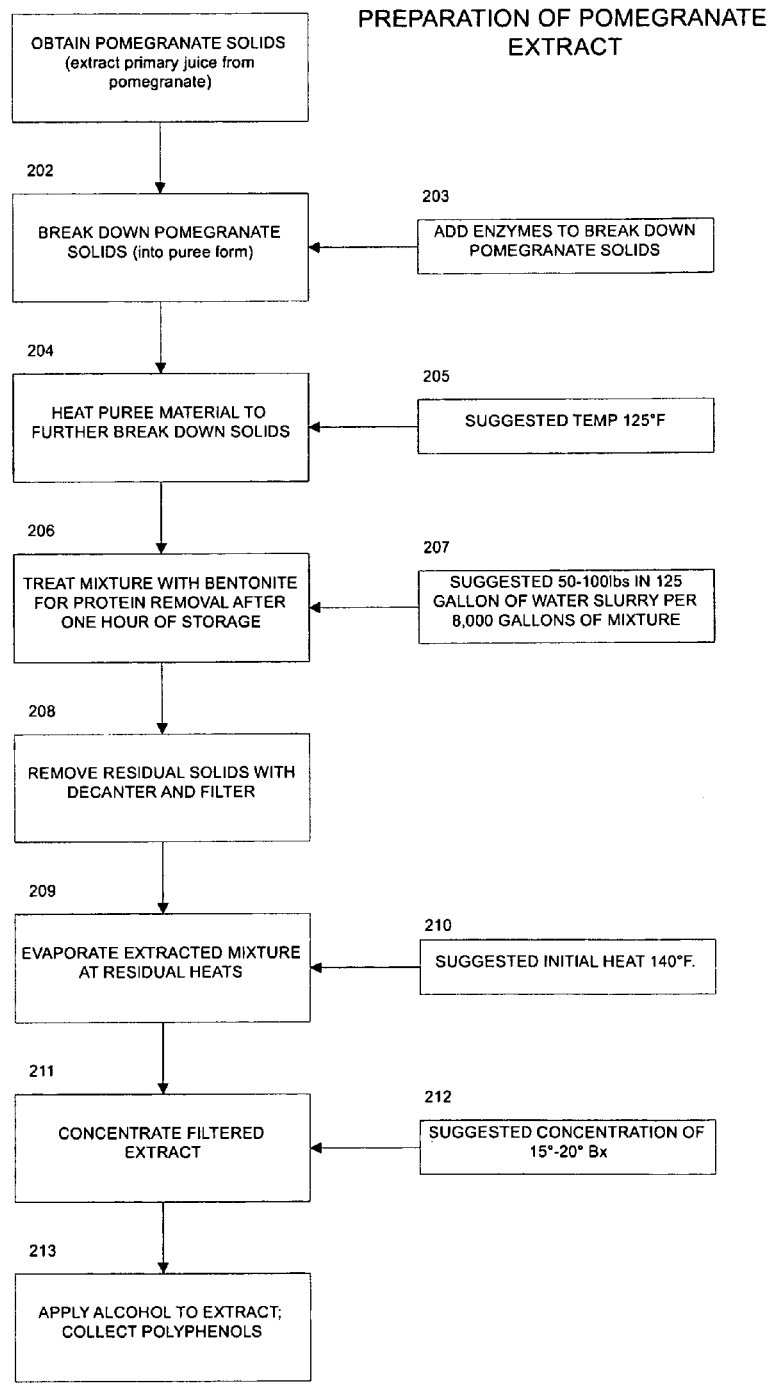
FIG. 2 illustrates an exemplary method for the preparation of a pomegranate extract.

The starting material for the production of the pomegranate dry composition is the pomegranate solids, which generally comprises the pericarp, the inner membrane and seed of the pomegranate. FIG. 2 shows an exemplary method for the preparation of a pomegranate extract. At 201 the pomegranate solids are obtained and collected after the primary juice from the arils is substantially expelled or otherwise removed from the pomegranate by pressing, crushing, or other methods of extracting pomegranate juice.

To assist with breaking down the colloidal structure of the remaining pomegranate solids, pomegranate solids may be further disrupted into finer particles, for example, using any milling or grinding techniques, shown at step 202. Step 203 shows that this step may be coupled with enzyme addition to release the remaining soluble solids from pomegranate solids. In one embodiment of this process, the pomegranate solids can be transferred to three Reitz Mills with ⅜ inch screens. The material in this specific example is then milled to a fine puree and heated to approximately 125° F. at step 204 and 205. This step, coupled with the following enzyme addition, assists in breaking down the colloidal structure of the remaining pomegranate solids, thereby releasing the remaining soluble solids.

As shown at exemplary step 204, the mixture is heated over a set period of time. In this example, the mixture is heated to a temperature of about 125° F. for two hours. Enzymes can be added to the mixture: in this example, three are added to the mixture, specifically pectinase (Rohapect® DA6L), cellulase/pectinase (Rohapect® CL), and hemi-cellulase/pectinase (Rohapect® B1L) but other enzymes may also be sufficient to achieve the same general result. These enzymes are helpful in liberating the remaining pomegranate soluble solids, such as sugars, minerals, anthocyanins, and remaining polyphenols.

The mixture may further be pumped from the point of extraction plant to a processing plant where it is treated. In this example, shown at step 206, the mixture was pumped from the extraction plant to the primary processing plant where it was held in the mash treatment tanks for approximately one hour. Further in this example, 50-100 pounds of bentonite in a 125 gallon of water slurry, per 8,000 gallons of the mixture, is added for protein removal after one hour. At step 208 solids are further removed from the treated extract, in this example the treated mixture was passed through a Westphalia 755 Decanter for this purpose, and residual insoluble material was discharged as waste. The extract is then filtered. In this example the liquid extract then exited the decanter and is filtered on Koch SUPER-COR® microfiltration membranes at a 500,00 Da molecular weight cut-off and then filtered again on Koch ultrafiltration membranes at a 100,000 or 200,000 Da molecular weight cut-off.

The extract is applied to an evaporator, in this example at step 209 the filtered liquid extract was then applied to a Schmidt-Bretten rising-film plate evaporator. Initial heat on this step is about 140° F., at step 210. The filtered liquid extract, at step 211, is concentrated to about 15° to 20° Bx.

The filtered liquid extract is maintained for example at the temperature of about 140° F. and then passed through a preheated 140° F. preparative column (4-foot diameter, 4-foot tall) packed with Amberlite™ FPX66 at the flow rate of two bed volumes an hour until the resins gets loaded. Portions of liquid effluent that indicate bleed-through of polyphenols are collected for subsequent loading step.

Further in this example, unbound material is removed. After the load step, for example, dilute aqueous alcohol (2% ethanol/$H_2O$) is passed through the preparative column at the flow rate of two bed volumes an hour to remove unbound material. Dilute aqueous alcohol effluent is discarded as a waste.

After the rinse step, concentrated aqueous alcohol (in this example 20% ethanol/$H_2O$) is applied to the resin at step 213 and the liquid eluate containing polyphenols collected. In an optional step, the liquid eluate can then enter through a distillation unit to remove and recover alcohol. The recovered alcohol may be reused for subsequent cycles of rinse and elution steps. The liquid eluate containing polyphenols may be used in one or more embodiments of the invention.

In an optional step, the liquid eluate containing polyphenols is transferred into a tray and dried in an oven at about 70°-80° C. After drying step, the resulting eluate is in the form of a dense powder, which may be used in one or more embodiments of the invention as the composition for administering to trigger the desired immunological response.

Figure 3:
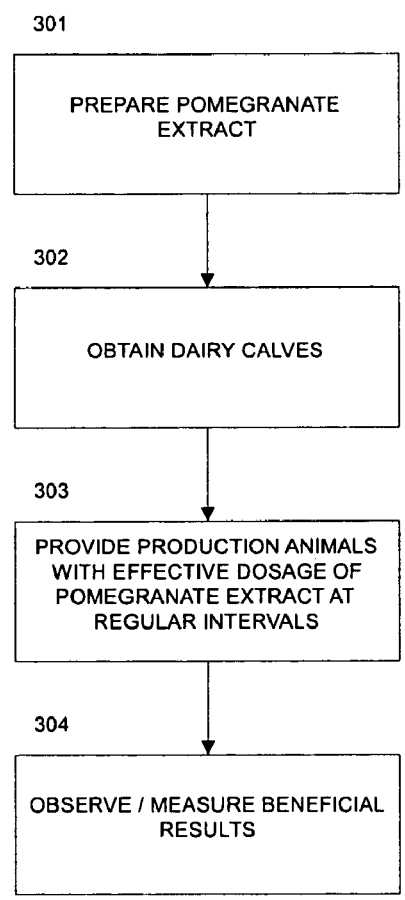
FIG. 3 shows a flow chart illustrating the timing, dosages and frequency for administering the pomegranate extract in accordance with at least one embodiment of the invention.

FIG. 3 describes the steps used in the following examples in providing a Pomegranate Extract to production animals, more specifically by way of example, dairy calves. At step 301, a pomegranate extract is prepared using the method illustrated in Example 1. Production animals, such as dairy calves, are obtained at 302 for the purposes of improving their immunology through nutritional augmentation. At step 303 the production animals are provided with a specific dosage of pomegranate extract that has been shown to provide beneficial results in production animals. In one embodiment of the invention the extract provided is made from the POM Wonderful varietal such as the one in POMx. At step 304 the beneficial results of administration of the pomegranate extract are observed in the production animals to which they were administered. Further to this, specific examples are now provided for the purpose of illustration in the following paragraphs.

Example 2

Effect of Feeding Pomegranate Extract to Dairy Calves

For purposes of illustrating effectiveness of one or more embodiments of the invention, the effects of feeding two levels of pomegranate extract ("5×"—5 g pomegranate extract/day or "10×"—10 g pomegranate extract/day) during the first 70 days of age on health of dairy calves is described. To support this illustration sixty Holstein male calves were assigned to one of four treatments (15 calves/treatment) in a randomized complete block design on the basis of study weight and serum protein on day 2 of age. Calves received 2 liters of colostrums within first 6 hours of birth and were transported to a site for housing in individual hutches. On day 2 of age, calves were weighted, a blood sample collected, and serum harvested for analysis of total protein using a clinical refractometer.

Calves were housed individually and fed 500 g of a milk replacer reconstituted into 4 liters of water divided into two feedings daily during the first 60 days of age. These calves were then weaned, in this example at 60 days of age.

In this example calves had ad libitum access to a starter grain throughout the study but exercising specific control over the amount of starter grain is considered within the scope and spirit of one or more embodiments of the invention. Dry matter (DM) content of milk and intake of calf grain were monitored daily to determine overall DM and nutrient intake of calves. Calves were fed with grain once daily to allow 3 to 5% orts and refusals were weighted daily.

Treatments: treatments were arranged in a 2×2 factorial, with pomegranate extract incorporated into the milk replacer and starter grain. Readers should note however that the concept described here is not limited to a specific type of food but that the pomegranate extract may be mixed into any food source generally feed to or preferred by the animal. Flavors to enhance the overall palatability of the food source may be added in addition to the pomegranate extract. This is generally helpful in cases where the bitterness of the pomegranate extract has an impact on the animals willingness to intake the food source. In this specific example, treatments were set up as: CM-CG—control milk, control grain (no pomegranate extract); PM-CG—pomegranate extract into milk replacer, control grain; CM-PG—control milk, pomegranate extract in grain; and, PM-PG—pomegranate extract into milk replacer and in grain.

To prepare PM (pomegranate extract into milk replacer): 5 grams (5×PM) or 10 grams (10×PM) of pomegranate extract prepared according to Example 1 was added to 500 grams of milk replacer reconstituted into 4 liters of water. Other pomegranate extracts however may be used and still accomplish effect of stimulating an immune response. Moreover the amount of pomegranate extract may be varied so long as the desired effect is achieved. This pomegranate extract can supplement reconstituted milk replacer divided into two feedings per calf each day during the first 60 days of age. The PM was prepared daily immediately prior to the feeding.

To prepare PG (pomegranate extract top dressed onto grain): pomegranate extract prepared according to Example 1 can be top dressed onto starter grain in the amount of approximately 5 grams pomegranate extract per calf each day (5×PG) or 10 grams of pomegranate extract per calf each day (10×PG). Any amount of pomegranate extract found to be beneficial may be used to implement one or more embodiments of the invention. Thus amounts other than what is specifically described here may achieve the desired beneficial result and as such these amounts would be considered an effective dose of pomegranate extract.

Feed Analyses: milk replacer and calf grain were sampled weekly and dried at 55° C. in an air circulating oven. Dried calf grain was ground in a Willey mill and frozen for later analyses. In the example study provided a monthly composite sample of dried milk and calf grain was analyzed for dry matter (DM) at 105° C., organic matter (OM), CP, crude fat, acid detergent fiber (ADF) and neutral detergent fiber (NDF) (Van Soest et al., 1991), starch, and macro and trace minerals using an A.R.L. ICP plasma emission spectrometer.

To determine the beneficial results obtained by adhering to feeding the pomegranate extract to production animals blood samples were evaluated and show to have positive effect on immune function.

Evaluation of Blood Samples

Evaluation of Rumen Fermentation and Development: in this study, blood samples (7 ml) were collected from all calves fed with starter grain (5×PG, 10×PG or CG) in accordance of the study of Example 2 every other week (days 14, 28, 42, 56, and 70 of age) by puncture of the jugular vein using Vacutainer tubes containing $K_2$ EDTA. After collection, samples were immediately placed on ice, transported to a laboratory, and then centrifuged at 2,000×g for 20 minutes for plasma separation. Plasmas were frozen at −25° C. for later analyses of β-OH-butyrate (BHBA) and glucose by direct measurement. Plasma BHBA concentrations are used as an indicator of active rumen fermentation and rumen development in pre-ruminant calves. The specific amounts and times may be altered or modified to produce the beneficial effect required by application of the composition.

Evaluation of Humoral Immunity: calves in the study of Example 2 received an intramuscular injection of 2 mL containing 500 mg of ovalbumin in a suspension with adjuvant and PBS at days 3, 21 and 42 of age and blood samples were collected immediately prior to each injection and again at day 56 of age. Blood samples (7 ml) were collected by puncture of the jugular vein using Vacutainer tubes containing no anticoagulant for separation of serum. Tubes were places at room temperature to allow blood to clot and samples were brought to the laboratory to be centrifuged at 2,000×g for 20 minutes for separation of serum. Serum samples were frozen at −25° C. for later analyses of anti-ovalbumin IgG by ELISA based on the method of Mallard et al. (1997) and later analyses of total IgG concentration by agar gel immunodiffusion.

Evaluation of Cellular Immunity: cell-mediated immunity was evaluated twice, at days 21 and 42 of age. Blood were collected (50 ml) from calves by puncture of the jugular vein using Vacutainer tubes containing $K_2$ EDTA and placed immediately on ice. Samples were transported to the laboratory for neutrophils isolation and phagocytosis and intracellular bacteria killing assays. After isolation, neutrophils were incubated in duplicates, one with a 1:3 ratio of a known strain of *Escherichia coli*. The neutrophil—*E. coli* suspension was stained with acridine orange and crystal violet to determine the proportions of live an dead bacteria using an epifluorescent microscope. The proportion of neutrophils with intracellular bacteria was evaluated for phagocytosis. Also, from those neutrophils that phagocytized bacteria, the proportion that killed bacteria was determined based on differential staining.

Table 1 illustrates the effect of feeding pomegranate extract to calves on cellular immunity by evaluating the phagocytic and killing ability of neutrophils. Neutrophil phagocytic ability (61.3 vs 62.0 vs 64.6%) and killing percentages (54.8 vs 53.4 vs 58.2%) were similar (P>0.65) for control (CG), 5×PG and 10×PG, respectively.

TABLE 1

Effect of feeding pomegranate extract to calves on phagocytic and killing ability of neutrophils

| | Treatment | | | P |
|---|---|---|---|---|
| | Control | 5 × PG | 10 × PG | Treatment |
| % Neutrophils phagocytizing[1] | 61.3 ± 4.6 | 62.0 ± 4.6 | 64.6 ± 5.0 | 0.81 |
| n Bacteria phagocytized | 162.4 ± 19.7 | 152.0 ± 19.9 | 146.8 ± 21.6 | 0.79 |
| n Intracellular bacteria/neutrophil[2] | 5.4 ± 0.5 | 4.9 ± 0.5 | 4.5 ± 0.5 | 0.28 |
| Neutrophils killing bacteria | | | | |
| % of all neutrophils[3] | 54.8 ± 4.5 | 53.4 ± 4.5 | 58.2 ± 4.9 | 0.65 |
| % of neutrophils phagocytizing[4] | 87.4 ± 2.3 | 85.7 ± 2.3 | 89.0 ± 2.5 | 0.48 |
| % Bacteria killed[5] | 72.4 ± 4.0 | 69.9 ± 4.0 | 76.8 ± 4.4 | 0.34 |

[1]Percentage of neutrophils containing at least one intracellular bacterium (live or dead).
[2]Number of bacteria phagocytized/number of neutrophils phagocytizing at least one bacterium.
[3]Percentage of all neutrophils containing at least one dead bacterium.
[4]Percentage of phagocytizing neutrophils containing at least one dead bacterium.
[5]Percentage of phagocytized bacteria dead.

Table 2 illustrates the effect of feeding pomegranate extract to calves on cytokine production by peripheral blood mononuclear cells (PBMC). The production of tumor-necrosis factor-alpha was similar among treatments, but a linear increase (P=0.05) in dose response manner of PBMC production of interferon gamma (102 vs 200 vs 297 pg/mL) and interleukin-4 (271 vs 432 vs 497 pg/mL) was observed.

IL-4 is a major stimulus for production of IgE and the development of $T_h2$ cells for defense against helminths and arthropods. It also antagoizes the effects of interferon-gamma and thus inhibits cell-mediated immunity. IL-4 is produced mainly by $T_h2$ cells and mast cells. IFN-gamma is the principal cytokine for activating macrophages. It also induces the production of MHC-I molecules, MHC-II molecules, and co-stimulatory molecules by APCs in order to promote cell-mediated immunity and activates and increases the antimicrobial and tumoricidal activity of monocytes, macrophages, neutrophils, and NK cells. IFN-gamma stimulates the differentiation of T4-lymphocytes into $T_h1$ cells and inhibits the proliferation of $T_h2$ cells; stimulates the production of IgG subclasses that activate the complement pathway and promote opsonization; and augments or inhibits other cytokine activities. As illustrated in Table 2, administration of pomegranate extract stimulated both T-helper cell subtypes $T_h1$ and $T_h2$ since IL-4 is produced by $T_h2$ cells and IFN-gamma stimulates $T_h1$ cells and inhibits $T_h2$ cells.

TABLE 2

Effect of feeding pomegranate extract to calves on cytokine production by peripheral blood mononuclear cells.

| Cytokine | Treatment | | | P |
|---|---|---|---|---|
| | Control | 5 × PG | 10 × PG | Control |
| Tumor necrosis factor-α (pg/$10^6$ cells) | 1036.6 ± 99.1 | 932.6 ± 108.0 | 1060.0 ± 101.6 | 0.54 |
| Interferon γ (pg/$10^6$ cells) | 102.2 ± 80.9 | 200.0 ± 89.6 | 296.8 ± 77.0 | 0.11 |
| Interleukin-4 (pg/$10^6$ cells) | 270.9 ± 94.2 | 431.8 ± 103.0 | 497.4 ± 91.9 | 0.09 |

FIG. 4 illustrates the effect of feeding pomegranate extract to calves on the rumen fermentation and development. Both the role of intestinal development and the process of transitioning calves from their neonatal reliance on nutrients supplied from milk to nutrients supplied from grain are of substantial economic importance to the producer. Development of a viable fermentation within the rumen is required to initiate the maturation of the rumen epithelia. This transition results in tremendous metabolic ramifications to calf growth rate, as tissues must convert from reliance on glucose supplied from milk to the metabolism of short-chain fatty acids as primary energy substrates. Polyphenols containing tannins were found to reduce protein digestion. As illustrated in FIG. 4, the administration of pomegranate extract did not adversely impact the rumen fermentation and development or interfere with nutrient digestibility.

FIG. 5 illustrates the effect of feeding pomegranate extract to animals on immune functions and humoral immunity. Serum anti-ovalbumin IgG increased with immunizations, and humoral immune response was enhanced (treatment× day, P=0.04) by administering pomegranate extract. Results indicate that adaptive immune response was enhanced by the administration of pomegranate extract. Since calves may be in a state of chronic inflammation due to infections, these immunoenhancing activities of pomegranate extract may result from an inhibition of inflammation leading to balanced immune function.

Example 3

Pomegranate extract can also be used as a treatment of mastitis. To illustrate this concept a 3-lactation cow in dry period with moderate mastitis was administered 10,000 mg/l of the pomegranate extract, once per day for 5 days. The pomegranate extract is formulated as a solution and administered by intramammary infusion. At the end of the treatment the cow is examined and the mastitis was eliminated.

Example 4

A 2-lactation cow without mastitis is administered a single dose of 10,000 mg/l of the pomegranate extract at the start of dry off period. The pomegranate extract is formulated as a solution and administered by intramammary infusion. Although mastitis occurs in other dry cows that are in the same herd but are not treated with the pomegranate extract, the cow treated is not infected. Because the sensitivity of the mammary region is of particular importance in production animals the pH of the pomegranate extract is adjusted to account for such sensitivities. To neutralize the effects of the injection the pH level can be adjusted to avoid irritation. Adjusting the PH level from 9 to 7 for instance helps alleviate irritation without causing a negative effect on the anti-microbial effects of the pomegranate extract. The specific levels may be replicated in varying amounts to have the beneficial effect replicated.

While the invention herein disclosed has been described by means of specific embodiments and applications thereof, numerous modifications and variations could be made thereto by those skilled in the art without departing from the scope of the invention set forth in the claims.

What is claimed is:

1. A method of reducing an involuntary cull in production animals comprising:
    administering to a production animal a composition comprising an effective amount of a pomegranate extract, wherein said pomegranate extract is derived from at least inner and outer peels of pomegranate fruit, and wherein an immunological response of said production animal is affected,
    wherein said effective amount administered ranges from 0.2 to 5% by weight of diet.

2. The method of claim 1, wherein said composition comprises animal feed, wherein said animal feed is mixed with said pomegranate extract.

3. The method of claim 2, wherein said wherein said pomegranate extract is added to said animal feed as a concentrated raw product.

4. The method of claim 2, wherein said wherein said pomegranate extract is added to said animal feed as a concentrated raw product with a protein.

5. The method of claim 1, wherein said effective amount reduces an involuntary cull of said production animal due to infection.

6. The method of claim 1, wherein said effective amount increases cytokine production by peripheral blood mononuclear cells in said production animal.

7. The method of claim 1, wherein said effective amount enhances a humoral immune response in said production animal.

8. The method of claim 1, wherein said effective amount is effective to treat mastitis in said production animal, wherein said production animal is a dairy animal with mastisis.

9. The method of claim 8, wherein said composition comprises a solution administered by intramammary injection.

10. The method of claim 9, wherein said composition is administered daily for five days.

11. The method of claim 9, wherein said composition comprises a polyphenol content equivalent to about 100 mg to about 10,000 mg of an extract comprising about 67.86 mg/ml polyphenols.

12. The method of claim 1, wherein said composition is administered to a dairy cow without mastitis by intramammary infusion as a preventative measure at the start of a dry off period of said dairy cow.

13. The method of claim 1, wherein said effective amount reduces an involuntary cull of said production animal due to disease.

14. The method of claim 1, wherein said effective amount reduces an involuntary cull of said production animal due to morbidity.

15. The method of claim 1, wherein said effective amount reduces an involuntary cull of said production animal due to mortality.

16. A method of reducing an involuntary cull in production animals comprising:
    administering to a production animal a composition comprising an effective amount of a pomegranate extract, wherein said pomegranate extract is derived from at least inner and outer peels of pomegranate fruit, and wherein an immunological response of said production animal is affected,
    wherein said composition comprises animal feed, wherein said animal feed is mixed with said pomegranate extract, and
    wherein said animal feed comprises milk replacer and wherein said production animal is unweaned.

17. A method of reducing an involuntary cull in production animals comprising:
    administering to a production animal a composition comprising an effective amount of a pomegranate extract, wherein said production animal is a mammal, wherein said pomegranate extract is derived from at least inner and outer peels of pomegranate fruit, and wherein an immunological response of said production animal is affected,
    wherein said composition comprises animal feed, wherein said animal feed is mixed with said pomegranate extract
    wherein said animal feed is suitable for any age of animal development of said production animal; and
    wherein said wherein said pomegranate extract is added to said animal feed as a concentrated raw product with a protein absorbed into a matrix.

\* \* \* \* \*